United States Patent [19]

Nedelec et al.

[11] 4,136,179

[45] Jan. 23, 1979

[54] 2,2-DIMETHYL-19-NOR-STEROIDS

[75] Inventors: Lucien Nedelec, Le Raincy; Vesperto Torelli, Maisons-Alfort; Robert Fournex, Paris, all of France

[73] Assignee: Roussel Uclaf, Paris, France

[21] Appl. No.: 831,254

[22] Filed: Sep. 7, 1977

[30] Foreign Application Priority Data

Sep. 17, 1976 [FR] France .................. 76 28026

[51] Int. Cl.$^2$ .................. A61K 31/56; C07J 17/00
[52] U.S. Cl. .................. 424/242; 260/239.55 C; 260/397.3; 260/397.45
[58] Field of Search .................. 424/242; 260/239.55 C, 260/397.3, 397.45

[56] References Cited

U.S. PATENT DOCUMENTS 3,708,474  1/1973  Nedelec et al. .................. 260/397.45
4,078,059  3/1978  Nedelec et al. .................. 424/242

FOREIGN PATENT DOCUMENTS 1067345  5/1967  United Kingdom .................. 260/397.3

*Primary Examiner*—Ethel G. Love
*Attorney, Agent, or Firm*—Hammond & Littell

[57] ABSTRACT

2,2-dimethyl-19-nor-steroids of the formula

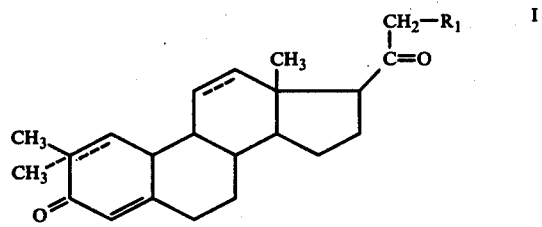

wherein $R_1$ is selected from the group consisting of hydrogen,

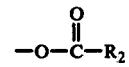

and $R_2$ is selected from the group consisting of hydrogen and hydrocarbon of 1 to 17 carbon atoms and the dotted lines indicate the optional presence of a double bond in 9(10) and 11(12) positions having antialdosteronic activity and an increased sodium diuresis with conservation of organic potassium and their preparation and novel intermediates.

17 Claims, No Drawings

2,2-DIMETHYL-19-NOR-STEROIDS

STATE OF THE ART

U.S. Pat. No. 3,708,474 describes 2,2-dimethyl trienic steroids which differ from the compounds of formula I by the substituent in the 17-position. U.S. Pat. No. 3,914,420 and commonly assigned U.S. Patent Application Ser. No. 719,138 filed Aug. 31, 1976, now U.S. Pat. No. 4,078,059 describe 2,2-dimethyl-$\Delta^4$-steroids which differ from the compounds of formula I by the substituents in the 10- and 17-positions.

OBJECTS OF THE INVENTION

It is an object of the invention to provide the novel 2,2-dimethyl steroids of formula I.

It is another object of the invention to provide a novel process and novel intermediates for the preparation of the steroids of formula I.

It is an additional object of the invention to provide novel antialdosterone compositions and to a novel method of relieving arterial hypertension and cardiac insufficiencies.

These and other objects and advantages of the invention will become obvious from the following detailed description.

THE INVENTION

The novel 2,2-dimethyl steroids of the invention have the formula

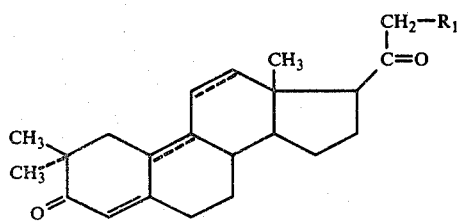

wherein $R_1$ is selected from the group consisting of hydrogen, —OH and

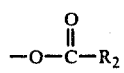

and $R_2$ is selected from the group consisting of hydrogen and hydrocarbon of 1 to 17 carbon atoms and the dotted lines indicate the optional presence of a double bond in 9(10) and 11(12) positions.

Examples of the hydrocarboncarboxylic acids from which the acyloxy of $R_1$ may be derived are saturated or unsaturated aliphatic and cycloaliphatic carboxylic acids such as alkanoic acids like acetic acid, propionic acid, butyric acid, isobutyric acid and undecylic acid; cycloalkylcarboxylic acids or cycloalkanoic acids such as cyclopropylcarboxylic acid, cyclopentylcarboxylic acid, cyclohexylcarboxylic acid, cyclopentylacetic acid, cyclohexylacetic acid, cyclopentylpropanoic acid and cyclohexylpropanoic acid; aromatic acids such as benzoic acid and phenylalkanoic acids such as phenylacetic acid and phenylpropanoic acid.

Among the preferred compounds of formula I are those wherein the B and C rings do not contain any ethylenic unsaturation, those wherein the C ring does not contain any ethylenic unsaturation and the B ring has ethylenic unsaturation in the 9(10) position and those wherein the B and C rings contain ethylenic unsaturation in the 9(10) and 11(12) positions, respectively. Equally preferred compounds of formula I are those wherein $R_1$ is hydrogen or —OH or acetoxy.

Specific compounds of formula I are 2,2-dimethyl-19-nor-$\Delta^4$-pregnene-3,20-dione, 2,2-dimethyl-21-acetoxy-19-nor-$\Delta^4$-pregnene-3,20-dione, 2,2-dimethyl-19-nor-$\Delta^4$-pregnene-21-ol-3,20-dione, 2,2-dimethyl-19-nor-$\Delta^{4,9}$-pregnadiene-3,20-dione, 2,2-dimethyl-21-acetoxy-19-nor-$\Delta^{4,9}$-pregnadiene-3,20-dione, 2,2-dimethyl-19-nor-$\Delta^{4,9}$-pregnadiene-21-ol-3,20-dione, 2,2-dimethyl-19-nor-$\Delta^{4,9,11}$-pregnatriene-3,20-dione, 2,2-dimethyl-21-acetoxy-19-nor-$\Delta^{4,9,11}$-pregnatriene-3,20-dione, 2,2-dimethyl-19-nor-$\Delta^{4,9,11}$-pregnatriene-21-ol-3,20-dione, 2,2-dimethyl-21-(butanoyloxy)-19-nor-$\Delta^4$-pregnene-3,20-dione and 2,2-dimethyl-21-propanoyloxy-19-nor-$\Delta^4$-pregnene-3,20-dione.

The novel process of the invention for the preparation of a compound of formula I comprises reacting a compound of the formula

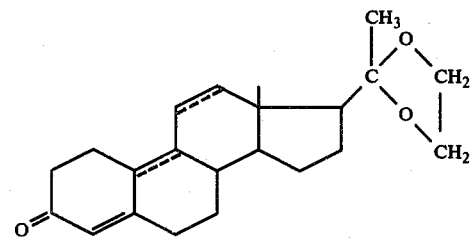

with a methyl halide in the presence of a basic agent at a low temperature to form a compound of the formula

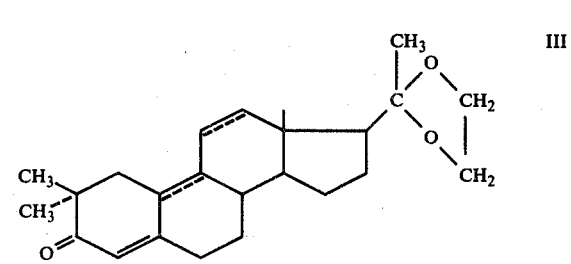

reacting the latter with a deketalization agent to form a compound of the formula

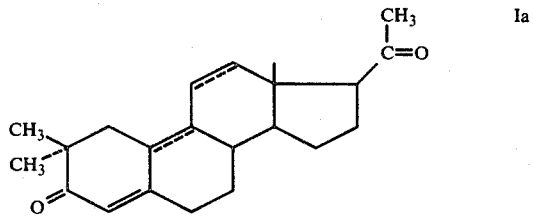

which, if desired, may be reacted with lead tetraacetate or with an oxalylation agent and then a halogenation agent to obtain the corresponding 21-halogenated compound which is then treated with an acetoxylation agent to form the compound of the formula

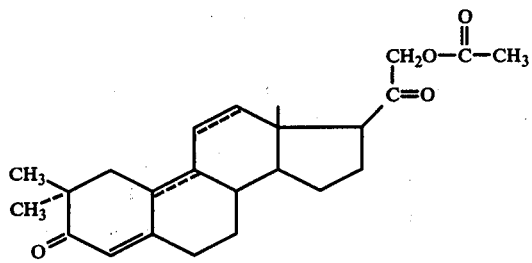

Ib which, if desired, may be treated with a saponification agent to obtain the compound of the formula

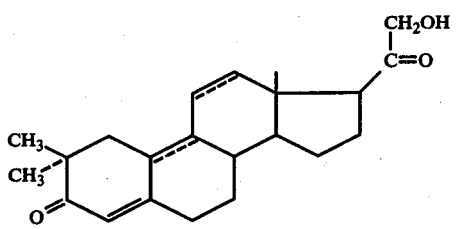

Ic which may be reacted with an acid of the formula $R_2$-COOH or a functional derivative thereof wherein $R_2$ has the above definition to obtain a compound of the formula

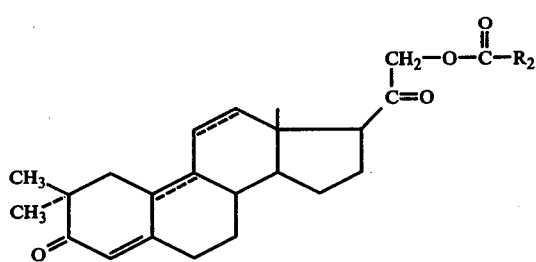

Id

In a preferred mode of the process, the methyl halide is methyl iodide and the basic agent is an alkali metal alcoholate such as potassium tert.-butylate and advantageously the reaction is effected in an aprotic solvent such as tetrahydrofuran. The deketalization agent is preferably an acid agent such as hydrochloric acid, acetic acid, sulfuric acid, citric acid or p-toluene sulfonic acid and the reaction is effected in one or more solvents such as methanol, ethanol, propanol or a ketone such as acetone.

The reaction with lead tetraacetate is preferably effected in the presence of boron trifluoride-ether complex and the preferred oxalylation agent is ethyl oxalate. The preferred halogenation agent is bromine or iodine and the preferred acetoxylation agent is potassium acetate. The saponification agent is preferably an alkali metal base such as sodium hydroxide, potassium hydroxide, potassium carbonate or potassium bicarbonate and the reaction is preferably effected in a lower alkanol solvent such as methanol or ethanol. The functional derivative of the acid is preferably the acid halide such as the bromide or chloride or the acid anhydride.

The starting compounds of formula II are novel intermediates and may be prepared from the corresponding 20-one compounds which are known and described in French Pat. Nos. 1,370,566, 1,369,324 and 1,468,636, for example.

Compounds of the Formula

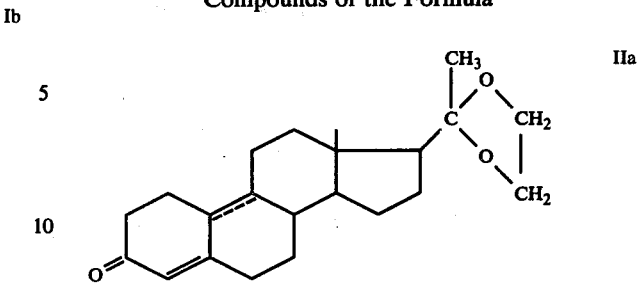

IIa may be prepared by forming a 3-enamino derivative of the corresponding 3,20-dione, treating the resulting compound with a strong acid to form the corresponding eniminium salt, reacting the latter with a ketalization agent and subjecting the resulting product to alkaline hydrolysis to form the compound of formula IIa.

Compounds of the Formula

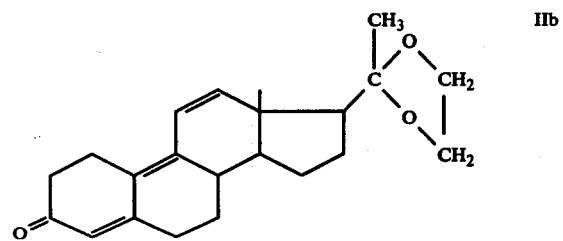

IIb may be prepared by reacting 19-nor-$\Delta^{4,9,11}$-pregnatriene-3,20-dione with a ketalization agent to obtain the corresponding 3,20-diketal and reacting the latter with a weak acid agent capable of selectively hydrolyzing the 3-ketal group.

The novel antialdosteronic compositions of the invention are comprised of an antialdosteronically effective amount of at least one compound of formula I and an inert pharmaceutical carrier or excipient. The compositions may be in the form of tablets, coated tablets, cachets, capsules, granules, emulsions, syrups, suppositories and injectable solutions or suspensions prepared in a known manner.

Examples of suitable excipients for the compositions of the invention are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, emulsifiers and dispersants.

The compositions of the invention have antagonistic activity to aldosterone and increase sodium diuresis with conservation of organic potassium to avoid secondary effects. They are useful for the treatment of arterial hypertension and cardiac insufficiencies. Particularly preferred are 2,2-dimethyl-19-nor-$\Delta^4$-pregnene-21-ol-3,20-dione and 2,2-dimethyl-19-nor-$\Delta^{4,9,11}$-pregnatriene-21-ol-3,20-dione.

The novel method of the invention for treating arterial hypertension and cardiac insufficiency in warm-blooded animals, including humans, comprises administering to warm-blooded animal a hypotensively effective amount of at least one compound of formula I. The compounds may be administered orally, rectally, transcutaneously or transveinously. The usual effective daily dose is 0,2 to 20 mg/kg depending upon the method of administration and the particular compound.

In the following examples there are described several preferred embodiments to illustrate the invention. However, it should be understood that the invention is not intended to be limited to the specific embodiments.

EXAMPLE 1

2,2-dimethyl-19-nor-$\Delta^4$-pregnene-3,20-dione

STEP A: 3-pyrrolidino-19-nor-$\Delta^{3,5}$-pregnadiene-20-one

A mixture of 8.3 g of 19-nor-$\Delta^4$-pregnene-3,20-dione, 33 ml of methanol and 8.3 ml of pyrrolidine was stirred at room temperature for 20 minutes and the mixture was iced for 2 hours and filtered under reduced pressure to obtain 9.76 g of 3-pyrrolidino-19-nor-$\Delta^{3,5}$-pregnadiene-20-one melting at 170° C.

STEP B: 20,20-ethylenedioxy-19-nor-$\Delta^4$-pregnene-3-one 10 ml of a solution of 1.9N hydrochloric acid in ethyl acetate was added to a solution of 5.9 g of the product of Step A in 15 ml of ethyl acetate and the mixture was evaporated to dryness. The residue was taken up in a mixture of 30 ml of ethylene glycol, 15 ml of ethyl orthoformate and 600 mg of p-toluene sulfonic acid monohydrate and the mixture was heated under nitrogen for one hour at 90° C. After cooling to room temperature, 12 ml of concentrated ammonium hydroxide and 30 ml of methanol were added thereto and the mixture was stirred for 16 hours. The mixture was diluted with water and was extracted with methylene chloride. The organic extracts were washed with water, dried and evaporated to dryness. The residue was chromatographed over silica gel and was eluted with a 9-1 benzene-ethyl acetate mixture to get 5.01g of 20,20-ethylenedioxy-19-nor-$\Delta^4$-pregnene-3-one melting at 135° C.

STEP C: 2,2-dimethyl-19-nor-$\Delta^4$-pregnene-3,20-dione 345 mg of the product of Step B were dissolved under nitrogen in 3 ml of tetrahydrofuran and 1.5 ml of methyl iodide and a solution of 700 mg of potassium tert.-butylate in 4 ml of anhydrous tetrahydrofuran was slowly added thereto over 15 minutes at −60° C. After 25 minutes, a solution of 450 mg of potassium tert.-butylate in 4 ml of tetrahydrofuran was added thereto and the mixture was stirred at −60° C. for 10 minutes. The mixture was acidified to a pH of 2 with concentrated hydrochloric acid and was diluted with water. The mixture was stirred for 10 minutes at room temperature and was extracted with methylene chloride. The organic extracts were evaporated to dryness and the residue was chromatographed over silica gel. Elution with a 9-1 benzene-ethyl acetate mixture yielded 228 mg of 2,2-dimethyl-19-nor-$\Delta^4$-pregnene-3,20-dione melting at 169° C.

EXAMPLE 2

2,2-dimethyl-21-acetoxy-19-nor-$\Delta^4$-pregnene-3,20-dione

STEP A: ethyl 2,2-dimethyl-19,21-dinor-$\Delta^4$-cholen-3,20,23-trione-oate 106 mg of sodium methylate and 0.75 ml of ethyl oxalate were added to a solution of 455 mg of 2,2-dimethyl-19-nor-$\Delta^4$-pregnene-3,20-dione and 4 ml of anhydrous benzene and the mixture was stirred at room temperature for one hour and was acidified with dilute hydrochloric acid. The organic phase was decanted, dried and evaporated to dryness to obtain ethyl 2,2-dimethyl-19,21-dinor-$\Delta^4$-cholen-3,20,23-trione-oate which was used as is for the next step.

STEP B: 2,2-dimethyl-21-acetoxy-19-nor-$\Delta^4$-pregnene-3,20-dione

A suspension of 6 ml of methanol and 1.17 ml of 1.18N potassium hydroxide in methanol and the product of A was stirred at −20° C. and then a solution of 350 mg of iodine in 7 ml of methanol was added dropwise thereto over 15 minutes. The mixture was stirred at −20° to −25° C. for one hour and then 1.4 ml of aqueous N potassium hydroxide were added thereto. The mixture was stirred another 5 minutes and then was diluted with water and extracted with methylene chloride. The dry extracts were dissolved in 12 ml of acetone and 1 g of anhydrous potassium acetate was added thereto. The mixture was refluxed under nitrogen for 1½ hours and was then cooled and diluted with water. The mixture was extracted with chloroform and the extract was chromatographed over silica gel. Elution with an 8-2 benzene-ethyl acetate mixture yielded 248 mg of 2,2-dimethyl-21-acetoxy-19-nor-$\Delta^4$-pregnene-3,20-dione melting at 110° C. and then 140° C. after crystallization from methanol.

EXAMPLE 3

2,2-dimethyl-19-nor-$\Delta^4$-pregnene-21-ol-3,20-dione

A suspension of 650 mg of the product of Example 2 in 13 ml of methanol was refluxed under nitrogen for 15 minutes and after the addition of 170 mg of potassium bicarbonate and 1.7 ml of water, the mixture was refluxed for another 40 minutes. The mixture was then acidified and diluted with water and was extracted with methylene chloride. The dried extract was chromatographed over silica gel and elution with an 8-2 benzene-ethyl acetate mixture resulted in a product which after crystallization from a methylene chloride-isopropyl ether mixture yielded 438 mg of 2,2-dimethyl-19-nor-$\Delta^4$-pregnene-21-ol-3,20-dione melting at 156° C.

EXAMPLE 4

2,2-dimethyl-19-nor-$\Delta^{4,9}$-pregnadiene-3,20-dione

STEP A: 3-pyrrolidino-19-nor-$\Delta^{3,5(10),9(11)}$-pregnatriene-20-one

A mixture of 9 g of 19-nor-$\Delta^{4,9}$-pregnadiene-3,20-dione in 9 ml of pyrrolidine and 45 ml of methanol was iced and filtered under reduced pressure. The recovered precipitate was washed and dried to obtain 9.3 g of 3-pyrrolidino-19-nor-$\Delta^{3,5(10),9(11)}$-pregnatriene-20-one melting at 174° C.

STEP B: 20,20-ethylenedioxy-19-nor-$\Delta^{4,9}$-pregnadiene-3-one 30 ml of a solution of 1.95 M of hydrochloric acid in ethyl acetate were added to a solution of 9.5 g of the product of Step A in 50 ml of chloroform and the mixture was evaporated to dryness under reduced pressure. The residue was dissolved under nitrogen in 45 ml of ethylene glycol and 950 mg of p-toluene sulfonic acid monohydrate and 22.5 ml of ethyl orthoformate were added thereto. The mixture was stirred at 80° to 90° C. for 90 minutes and after cooling the mixture to room temperature, 30 ml of ammonium hydroxide, 15 ml of water and 90 ml of methanol were added thereto. The mixture was stirred at room temperature for one hour and was diluted with water. The mixture was extracted with methylene chloride. The extracts were evaporated to dryness and the residue was chromatographed over silica gel. Elution with an 8-2 benzene-ethyl acetate mixture yield 7.03 g of 20,20-ethylenedioxy-19-nor-$\Delta^{4,9}$-pregnadiene-3-one which melted at 143° C. after crystallization from isopropyl ether.

STEP C: 2,2-dimethyl-19-nor-$\Delta^{4,9}$-pregnadiene-3-one

A mixture of 7.32 g of 20,20-ethylenedioxy-19-nor-$\Delta^{4,9}$-pregnadiene-3-one, 50 ml of tetrahydrofuran and 15 ml of methyl iodide was stirred under nitrogen at −60° C. and a solution of 10 g of potassium tert.-butylate in 50 ml of tetrahydrofuran was added over 30 minutes. The mixture was stirred for 40 minutes at −60° C. after the addition and then 40 ml of 5N hydrochloric acid were added thereto. The temperature returned to room temperature and the mixture was then stirred for an hour and was diluted with water. The mixture was extracted with ethyl acetate and the dried extracts were chromatographed over silica gel. Elution with benzene and then benzene containing 5% of ethyl acetate resulted in 4.14 g of 2,2-dimethyl-19-nor-$\Delta^{4,9}$-pregnadiene-3,20-dione which after crystallization from a mixture of isopropyl ether and petroleum ether (b.p. = 40°–70° C.) melted at 92° C.

EXAMPLE 5

2,2-dimethyl-21-acetoxy-19-nor-$\Delta^{4,9}$-pregnadiene-3,20-dione

STEP A: ethyl 2,2-dimethyl-19,21-dinor-$\Delta^{4,9}$-choladien-3,20,23-trione-oate 5 ml of ethyl oxalate and 1.1 g of a 50% sodium hydroxide suspension in oil were added with stirring under nitrogen to a solution of 4.9 g of the product of Example 4 in 50 ml of anhydrous benzene and the mixture was stirred for one hour and was filtered. 40 ml of 2N hydrochloric acid were added to the filtrate and the mixture was stirred for 20 minutes. The organic phase was decanted, dried and distilled to dryness to obtain ethyl 2,2-dimethyl-19,21-dinor-$\Delta^{4,9}$-choladien-3,20,23-trione-oate melting at 110°–115° C.

STEP B: 2,2-dimethyl-21-acetoxy-19-nor-$\Delta^{4,9}$-pregnadiene-3,20-dione

The product of Step A was treated according to the process of Step B in Example 2 to obtain 2,2-dimethyl-21-acetoxy-19-nor-$\Delta^{4,9}$-pregnadiene-3,20-dione melting at 142° C. of the purification by silica gel chromatography and crystallization from methanol.

EXAMPLE 6

2,2-dimethyl-19-nor-$\Delta^{4,9}$-pregnadiene-21-ol-3,20-dione

A solution of 2.5 g of the product of Example 5 in 50 ml of methanol was refluxed under nitrogen with stirring and a solution of 700 mg of potassium bicarbonate in 7 ml of distilled water was added thereto. The mixture was refluxed for 75 minutes and cooled to room temperature. 0.5 ml of acetic acid were added and the mixture was concentrated to a small volume and was diluted with water. The mixture was extracted with ethyl acetate and the dried extract was chromatographed over silica gel. Elution with a 9-1 benzene-ethyl acetate mixture yielded after crystallization from a solution of 30 volumes of ethyl ether concentrated to 5 volumes 1.41 g of 2,2-dimethyl-19-nor-$\Delta^{4,9}$-pregnadiene-21-ol-3,20-dione melting at 110° C.

EXAMPLE 7

2,2-dimethyl-19-nor-$\Delta^{4,9,11}$-pregnatriene-3,20-dione

STEP A: 20,20-ethylenedioxy-19-nor-$\Delta^{4,9,11}$-pregnatriene-3-one

A solution of 4 g of pyridine hydrochloride and 20 ml of ethylene glycol were added to a solution of 4 g of 19-nor-$\Delta^{4,9,11}$-pregnatriene-3,20-dione in 120 ml of chloroform and the mixture was refluxed under nitrogen for 8 hours. The mixture was cooled to room temperature and was poured into a saturated sodium bicarbonate solution. The organic phase was decanted, washed with water, dried and evaporated to dryness and the residue was dissolved in 132 ml of methanol, 26.3 ml of water and 1.3 g of citric acid. The solution was stirred at room temperature for 20 minutes and was poured into a saturated sodium bicarbonate solution. The mixture was extracted with methylene chloride and the dried extract was chromatographed over silica gel. Elution with an 80-20-0.5 benzene ethyl acetate-triethylamine yielded after crystallization from isopropyl ether 2.390 g of 20,20-ethylenedioxy-19-nor-$\Delta^{4,9,11}$-pregnatriene-3-one melting at 116° C.

STEP B: 2,2-dimethyl-20,20-ethylenedioxy-19-nor-$\Delta^{4,9,11}$-pregnatriene-3-one 1 ml of methyl iodide was added to a solution of 510 mg of 20,20-ethylenedioxy-19-nor-$\Delta^{4,9,11}$-pregnatriene-3-one in 3 ml of anhydrous tetrahydrofuran and the mixture was cooled to −60° C. under nitrogen. A solution of 700 mg of potassium tert.-butylate was added at −60° C. and the mixture was stirred at −60° C. for one hour. The mixture was poured into a solution saturated with ammonium chloride and was extracted with ethyl acetate. The organic extracts were washed with water, dried and evaporated to dryness under reduced pressure. The residue was chromatographed over silica gel and was eluted with a 95-5 benzene-ethyl acetate mixture to obtain 380 mg of 20,20-ethylenedioxy-19-nor-$\Delta^{4,9,11}$-pregnatriene-3-one melting at 112°–114° C.

STEP C: 2,2-dimethyl-19-nor-$\Delta^{4,9,11}$-pregnatriene-3,20-dione 5 ml of 5N hydrochloric acid were added to a solution of 3.5 g of the product of Step A in 25 ml of acetone and the mixture was held for an hour at room temperature was diluted with an excess of saturated sodium bicarbonate solution. The mixture was extracted with chloroform and the extract was evaporated to dryness to obtain 3.1 g of raw product. The latter was chromatographed over silica gel and was eluted with a 9-1 benzene-ethyl acetate to obtain 2,7 g of 2,2-dimethyl-19-nor-$\Delta^{4,9,11}$-pregnatriene-3,20-dione which melted at 110° C. after crystallization from isopropyl ether.

EXAMPLE 8

2,2-dimethyl-21-acetoxy-19-nor-$\Delta^{4,9,11}$-pregnatriene-3,20-dione

STEP A: ethyl 2,2-dimethyl-19,21-dinor-$\Delta^{4,9,11}$-cholatriene-3,20,23-trione-oate 1 ml of ethyl oxalate and 200 mg of sodium hydride (50% suspension in oil) were added to a solution of 1 g of 2,2-dimethyl-19-nor-$\Delta^{4,9,11}$-pregnatriene-3,20-dione in 10 ml of benzene and the mixture was stirred at room temperature under nitrogen for 90 minutes. The mixture was diluted with an excess of 2N hydrochloric acid and the mixture was stirred, decanted and extracted with ethyl acetate. The organic extracts were washed with water, dried and evaporated to dryness under reduced pressure. The residue was chromatographed over silica gel and was eluted with a 8-2 benzene-ethyl acetate mixture to obtain 1.08 g of ethyl 2,2-dimethyl-19,21-dinor-$\Delta^{4,9,11}$-cholatrien-3,20,23-trione-oate which was used as is for the next step.

STEP B: 2,2-dimethyl-21-acetoxy-19-nor-$\Delta^{4,9,11}$-pregnatriene-3,20-dione Using the procedure of Step B of Example 2, the product of Step A was reacted to obtain 1g of 2,2-dimethyl-21-acetoxy-19-nor-$\Delta^{4,9,11}$-pregnatriene-3,20-dione.

EXAMPLE 9

2,2-dimethyl-19-nor-$\Delta^{4,9,11}$-pregnatriene-21-ol-3,20-dione

A mixture of 2.35 g of the product of Example 8 in 45 ml of methanol was refluxed under nitrogen and a solution of 650 mg of potassium bicarbonate in 6.5 ml of water was added thereto. The mixture was refluxed for an hour, was cooled and was diluted with water. The pH was adjusted to 4 by addition of acetic acid and the mixture was extracted with ethyl acetate. The organic extracts were evaporated to dryness and the residue was chromatographed over silica gel. Elution with an 8-2 benzene-ethyl acetate mixture yielded 720 mg of product which was crystallized from a mixture of methylene chloride and petroleum ether (b.p. = 40°-70° C.) to obtain 637 mg of 2,2-dimethyl-19-nor-$\Delta^{4,9,11}$-pregnatriene-21-ol-3,20-dione melting at 153° C.

EXAMPLE 10

Tablets were prepared containing 50 mg of the product of Example 3 and sufficient excipient of talc, starch and magnesium stearate.

PHARMACOLOGICAL STUDY

Anti-aldosterone Activity

Male rats of the Sprague-Dawley strain weighing about 180 g were surrenalectomized and at that moment, the rats received with their drinking water physiological serum. On the 4th day, the animals were fasted for 16 hours and then received as drinking water water containing 5% glucose. The test product was administered orally at the end of 16 hours in the form of a suspension in 0.25% carboxymethylcellulose. One hour after the administration of the product, they received intraperitoneally a surcharge of aqueous sodium chloride at a rate of 5 ml per 100 g of body weight of 9% physiological serum and subcutaneously 1 μg/kg of an alcoholic solution of 2.5% of aldosterone acetate. The animals were placed in diuresis cages without food or drink for 4 hours. At the end of this time, a miction was forced by pressure on the bladder and the volume of urine was adjusted to 50 ml and the amount of sodium and potassium was determined with an autoanalyser. The results expressed as the percentage of inhibition of the activity of 1 μg/kg of aldosterone monoacetate injected subcutaneously with the ratio of $$\frac{\text{Sodium concentration}}{\text{Potassium concentration}}$$

in the surrenalectomized rats is reported in the following Table.

| Product of Example | Oral dose in mg/kg | % inhibition |
|---|---|---|
| 3 | 5 | 50 |
| 9 | 10 | 91 |

The results of the Table show that the products of Examples 3 and 9 present an interesting antialdosterone activity when orally administered.

Various modifications of the products and processes of the invention may be made without departing from the spirit or scope thereof and it is to be understood that the invention is to be limited only as defined in the appended claims.

We claim:

1. A compound of the formula

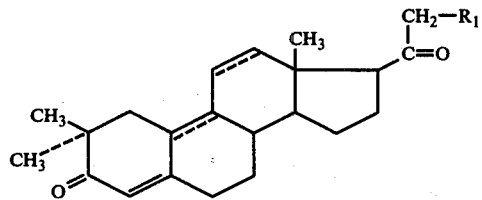

wherein $R_1$ is selected from the group consisting of hydrogen, —OH and

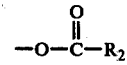

and $R_2$ is selected from the group consisting of hydrogen and hydrocarbon of 1 to 17 carbon atoms and the dotted lines indicate the optional presence of a double bond in 9(10) and 11(12) positions, with the proviso that when the C ring is unsaturated, the B ring is unsaturated.

2. A compound of claim 1 wherein the B and C rings do not have any ethylenic unsaturation.

3. A compound of claim 1 wherein the C ring is saturated and the B ring has ethylenic unsaturation in the 9(10) position.

4. A compound of claim 1 wherein the B and C ring have ethylenic unsaturation in the 9(10) and 11(12) positions.

5. A compound of claim 1 wherein $R_1$ is hydrogen.

6. A compound of claim 1 wherein $R_1$ is —OH.

7. A compound of claim 1 wherein $R_1$ is acetoxy.

8. A compound of claim 1 which is 2,2-dimethyl-19-nor-$\Delta^4$-pregnene-21-ol-3,20-dione.

9. A compound of claim 1 which is 2,2-dimethyl-19-nor-$\Delta^{4,9,11}$-pregnatriene-21-ol-3,20-dione.

10. An antialdosteronic composition comprising an antialdosteronically effective amount of at least one compound of claim 1 and an inert pharmaceutical carrier.

11. A composition of claim 10 wherein the compound is 2,2-dimethyl-19-nor-$\Delta^4$-pregnene-21-ol-3,20-dione.

12. A composition of claim 10 wherein the compound is 2,2-dimethyl-19-nor-$\Delta^{4,9,11}$-pregnatriene-21-ol-3,20-dione.

13. A method of treating arterial hypertension and cardiac insufficiency in warm-blooded animals comprising administering to warm-blooded animals an amount of at least one compound of claim 1 to relieve arterial hypertension and cardiac insufficiency.

14. The method of claim 13 wherein the compound is 2,2-dimethyl-19-nor-Δ⁴-pregnene-21-ol-3,20-dione.

15. The method of claim 13 wherein the compound is 2,2-dimethyl-19-nor-Δ$^{4,9,11}$-pregnatriene-21-ol-3,20-dione.

16. A compound of the formula

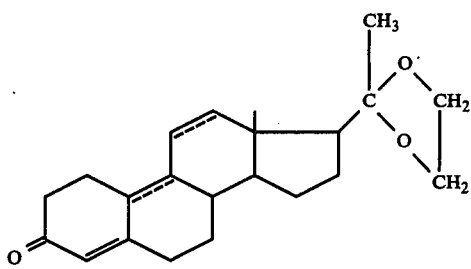

wherein the dotted lines indicate the optional presence of a double bond.

17. A process for the preparation of a compound of claim 1 comprising reacting a compound of the formula

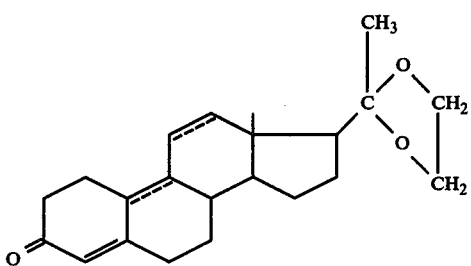

with a methyl halide in the presence of a basic agent at a low temperature to form a compound of the formula

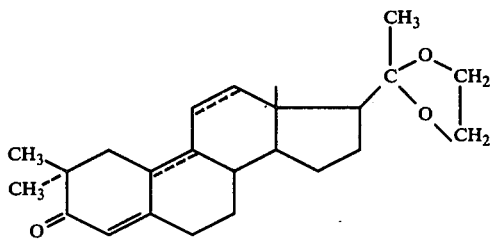

reacting the latter with a deketalization agent to form a compound of the formula

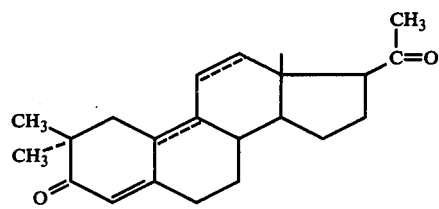

which, if desired, may be reacted with lead tetraacetate or with an oxalylation agent and then a halogenation agent to obtain the corresponding 21-halogenated compound which is then treated with ethyl oxalate to form the compound of the formula

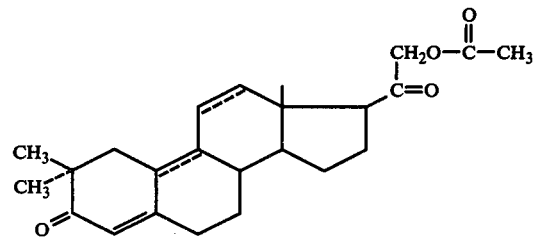

which, if desired, may be treated with a saponification agent to obtain the compound of the formula

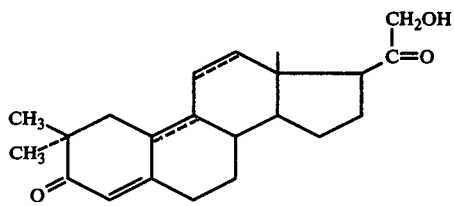

which may be reacted with an acid of the formula $R_2$-COOH or a functional derivative thereof wherein $R_2$ has the above definition to obtain a compound of the formula

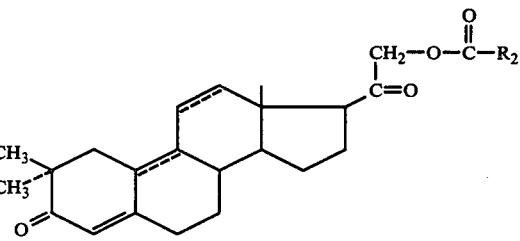

* * * * *